United States Patent [19]

Schmidt

[11] 4,404,209

[45] Sep. 13, 1983

[54] ANALGESIC MIXTURE OF NALBUPHINE AND SULINDAC

[75] Inventor: William K. Schmidt, Wilmington, Del.

[73] Assignee: E. I. Du Pont de Nemours and Company, Wilmington, Del.

[21] Appl. No.: 393,804

[22] Filed: Jun. 30, 1982

[51] Int. Cl.$^3$ .................. A61K 31/19; A61K 31/185; A61K 31/485
[52] U.S. Cl. .................................. 424/260; 424/315; 424/317
[58] Field of Search .................. 424/260, 315, 317

[56] References Cited

U.S. PATENT DOCUMENTS

| 3,393,197 | 7/1968 | Pachter et al. | 424/260 |
| 3,654,349 | 4/1972 | Shen et al. | 424/248.5 |
| 4,207,340 | 6/1980 | Gardocki | 424/317 |
| 4,237,140 | 12/1980 | Dudjinski | 424/260 |
| 4,282,215 | 8/1981 | Dudjinski et al. | 424/260 |

Primary Examiner—Stanley J. Friedman

[57] ABSTRACT

Pharmaceutical compositions of nalbuphine and sulindac have been found to exhibit unexpectedly enhanced analgesic activity by applying an analysis model which considers data characterizing the analgesic effect of both the pure components as well as the fixed dose ratio combinations. This synergism enables the use of lower doses of either or both drugs with a concomitant reduction in risk of possible side effects.

16 Claims, 1 Drawing Figure

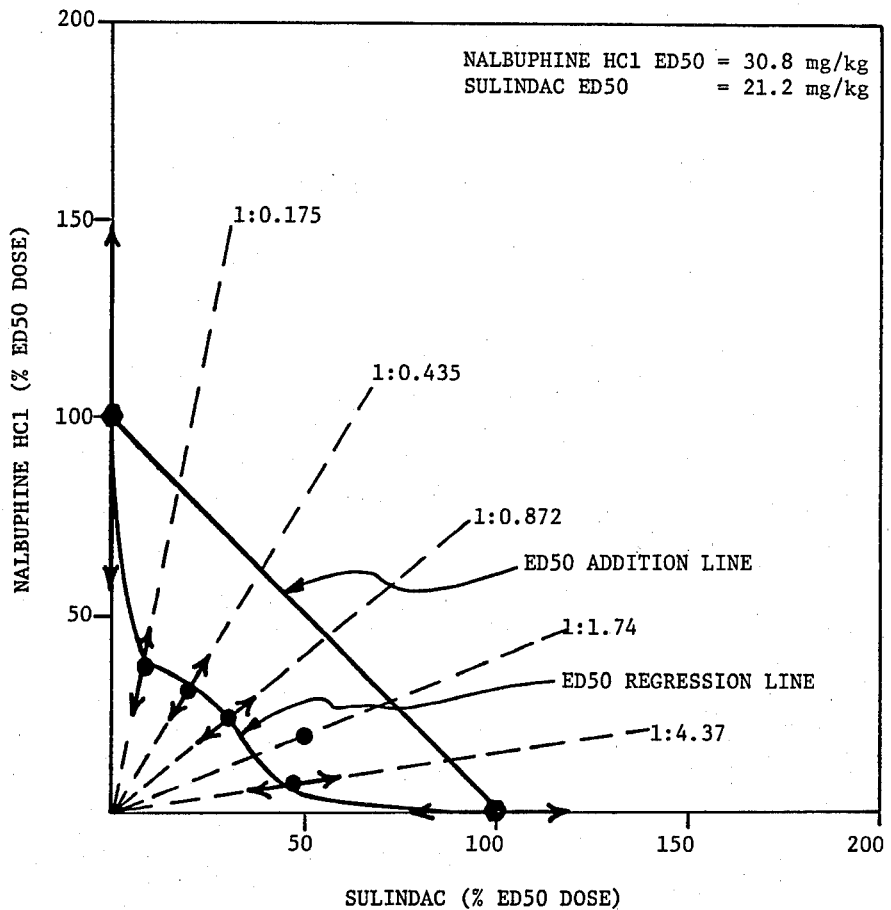

ANALGESIC MIXTURE OF NALBUPHINE AND SULINDAC

TECHNICAL FIELD

This invention relates to a pharmaceutical composition of nalbuphine and sulindac having analgesic activity in mammals, and to a method of use of the composition to alleviate pain in mammals.

BACKGROUND OF THE INVENTION

More active analgesic combinations are in constant demand because they offer the attractive possibility of relieving pain with reduced dosages thereby diminishing the expected side effects and toxicity that would result from the otherwise required higher dosages.

U.S. Pat. No. 3,393,197, issued to Pachter and Matossian on July 16, 1968, discloses N-substituted-14-hydroxydihydronormorphines, including the N-cyclobutylmethyl derivative, commonly called nalbuphine:

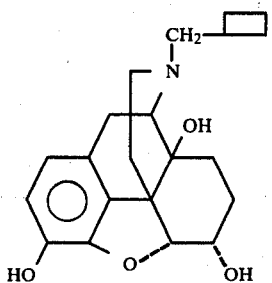

Pachter and Matossian and others, such as H. W. Elliott, et al., *J. Med.* (Basel), 1, 74–89 (1970); H. Blumberg, et al., *Pharmacologist*, 10, 189 (Fall 1968); P. Roberts, *Drugs of the future*, 2, 613–5 (1977), disclose the use of nalbuphine as an analgesic for the control of moderate to severe pain.

U.S. Pat. No. 4,237,140, issued to J. R. Dudzinski on Dec. 2, 1980, describes an analgesic mixture of nalbuphine and acetaminophen. U.S. Pat. No. 4,282,215, issued to J. R. Dudzinski and W. K. Schmidt on Aug. 4, 1981, describes an analgesic mixture of nalbuphine and aspirin.

U.S. Pat. Nos. 3,654,349 and 3,647,858 issued to Shen et al. and Hinckley et al., respectively, disclose the synthesis and analgesic utility of (Z)-5-fluoro-2-methyl-1-{[4-(methylsulfinyl)phenyl]methylene}-1H-indene-3-acetic acid, commonly called sulindac:

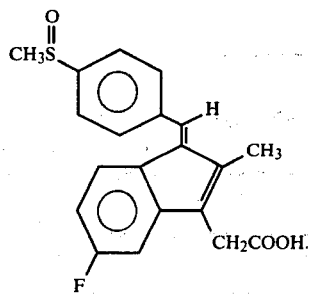

Van Arman et al., *Fed. Proc.*, 31, 577 (1972) disclose the pharmacological properties and metabolism of sulindac. U.S. Pat. No. 4,207,340 issued to J. F. Gardocki describes an analgesic mixture of sunlindac and acetaminophen.

SUMMARY OF THE INVENTION

It has now been found that combinations of nalbuphine and sulindac provide unexpectedly enhanced analgesic activity. Specifically, a pharmaceutical composition comprising a combination of synergistically effective analgesic amounts of nalbuphine, or a pharmaceutically suitable salt thereof, and sulindac, or a pharmaceutically suitable salt thereof, has been found to provide enhanced pain relief in mammals. Another aspect of the invention comprises the method of alleviating pain in a mammal by administering an effective analgesic amount of the composition described above to the mammal.

BRIEF DESCRIPTION OF THE DRAWING

The FIGURE is an isobologram plot characterizing effective pain relieving doses which produce analgetic responses in one half the mice subjected to the phenyl-p-benzoquinone induced writhing test at various dose ratios of nalbuphine and sulindac.

DETAILED DESCRIPTION OF THE INVENTION

Nalbuphine, which has the chemical name (−)-17-(cyclobutylmethyl)-4,5α-epoxymorphinan-3,6α,14-triol, and its preparation are described in U.S. Pat. No. 3,393,197, the disclosure of which is hereby incorporated by reference. Sulindac, which has the chemical name (Z)-5-fluoro-2-methyl-1-{[4-(methylsulfinyl)phenyl]methylene}-1H-indene-3-acetic acid, and its preparation are described in U.S. Pat. Nos. 3,654,349 and 3,647,858, the disclosures of which are hereby incorporated by reference. When the terms nalbuphine or sulindac are used herein, it is to be understood that any of the pharmaceutically suitable salts thereof which have analgesic properties in man and other mammals are included by the term. For nalbuphine, such salts include the hydrochloride, hydrobromide, hydroiodide, sulfate, bisulfate, nitrate, citrate, tartrate, bitartrate, phosphate, malate, maleate, fumarate, succinate, acetate and pamoate, while for sulindac, pharmaceutically suitable salts would include those of calcium, potassium, and sodium.

In the composition of the invention, nalbuphine and sulindac are combined and have been utilized at dose ratios based on weight of nalbuphine to sulindac of from 1:0.175 to 1:4.37 in mice subjected to the phenyl-p-benzoquinone induced writhing test to establish analgetic effectiveness. The phenyl-p-benzoquinone induced writhing test in mice [H. Blumberg et al., Proc. Soc. Exp. Biol. Med., 118, 763–766 (1965)] is a standard procedure for detecting and comparing the analgetic activity of different classes of analgesic drugs with a good correlation with human analgetic activity. Data for the mouse, as presented in the isobologram, can be translated to other species where the orally effective analgesic dose of the individual compounds is known or can be estimated. The method simply consists of reading the % ED50 DOSE for each dose ratio on the best fit regression analysis curve from the mouse isobologram, multiplying each component by its effective species dose, and then forming the ratio of the amount of nalbuphine to sulindac. This basic correlation for analgesic properties enables estimation of the range of human effectiveness. [E. W. Pelikan, The Pharmacologist, 1, 73 (1959).]

Application of an equieffective dose substitution model and a curvilinear regression analysis utilizing all the data for the individual compounds and various dose ratios establishes the existence of unexpectedly enhanced analgetic activity of combinations of nalbuphine and sulindac, i.e., the resulting activity is greater than the activity expected from the sum of the activities of the individual components.

The composition of the invention presents the opportunity of obtaining relief from pain with reduced dosages of nalbuphine and sulindac, thereby diminishing the side effects and toxicity which would result from the otherwise required amounts of the individual drug components.

DOSAGE FORMS

The combination of analgetic agents of the invention can be administered to treat pain by any means that produces contact of the active agent with the agent's site of action in the body of a mammal. The composition of the invention can be administered by any conventional means available for use in conjunction with pharmaceuticals. It can be administered alone, but is generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage can be such that the active ingredient is administered at a daily dosage of from about 0.25 to 7.50 milligrams per kilogram (mg/kg) of body weight of nalbuphine and from about 1.0 to 13 mg/kg of sulindac. Ordinarily, administration of the composition of the invention in divided doses 2-5 times a day or in a sustained release form is effective to obtain desired results.

Dosage forms (compositions) suitable for internal administration contain from about 15 milligrams to about 600 milligrams of active ingredients per unit. In these pharmaceutical compositions the active ingredients will ordinarily be present in an amount of about 0.5-95% by weight based on the total weight of the composition.

The active ingredients can be administered orally in solid dosage forms, such as capsules, tablets, and powders, or in liquid dosage forms, such as elixirs, syrups, and suspensions.

Gelatin capsules contain the active ingredients and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

Suitable pharmaceutical carriers are described in *Remington's Pharmaceutical Sciences*, A. Osol, a standard reference text in this field.

Useful pharmaceutical dosage-forms for administration of the composition of the invention can be illustrated by the following examples.

EXAMPLE 1

| Nalbuphine/Sulindac Tablets (30/30 mg) | |
|---|---|
| Formula | mg/Tablet |
| Nalbuphine HCl | 30.0 |
| Sulindac | 30.0 |
| Microcrystalline Cellulose | 170.0 |
| Starch, modified | 16.0 |
| Stearic Acid | 4.0 |
| | 250.0 |

EXAMPLE 2

| Nalbuphine/Sulindac Tablets (30/150 mg) | |
|---|---|
| Formula | mg/Tablet |
| Nalbuphine HCl | 30.0 |
| Sulindac | 150.0 |
| Microcrystalline Cellulose | 150.0 |
| Starch, modified | 14.0 |
| Stearic Acid | 6.0 |
| | 350.0 |

EXAMPLE 3

| Nalbuphine/Sulindac Tablets (7.5/300 mg) | |
|---|---|
| Formula | mg/Tablet |
| Nalbuphine HCl | 7.5 |
| Sulindac | 300.0 |
| Microcrystalline Cellulose | 212.5 |
| Starch, modified | 22.0 |
| Stearic Acid | 8.0 |
| | 550.0 |

EXAMPLE 4

| Nalbuphine/Sulindac Capsules (30/30 mg) | |
|---|---|
| Formula | mg/Capsule |
| Nalbuphine HCl | 30.0 |
| Sulindac | 30.0 |
| Microcrystalline Cellulose | 170.0 |
| Starch, modified | 112.0 |
| Starch | 8.0 |
| | 350.0 |

EXAMPLE 5

| Nalbuphine/Sulindac Capsules (30/150 mg) | |
|---|---|
| Formula | mg/Capsule |
| Nalbuphine HCl | 30.0 |
| Sulindac | 150.0 |
| Microcrystalline Cellulose | 150.0 |
| Starch, modified | 12.0 |
| Starch | 8.0 |
| | 350.0 |

EXAMPLE 6

| Nalbuphine/Sulindac Capsules (7.5/300 mg) | |
|---|---|
| Formula | mg/Capsule |
| Nalbuphine HCl | 7.5 |
| Sulindac | 300.0 |
| Microcrystalline Cellulose | 110.0 |
| Starch, modified | 9.5 |
| Starch | 8.0 |
| | 435.0 |

TEST METHODS

The unexpectedly enhanced analgetic activity obtained in the method of the invention is evidenced by tests conducted on mice. Male $CF_1$ mice obtained from Charles River Breeding Laboratories, fasted for 16–22 hours and weighing 18–22 g at the time of testing are used throughout. All mice are dosed sequentially by the oral route with suspensions of sulindac and/or of nalbuphine hydrochloride solutions. A dosing volume of 10 ml/kg is used for each sequential solution or suspension. It will be appreciated by those skilled in the art that the enhanced activity will be obtained whether the sulindac and nalbuphine are administered simultaneously as a mixture or sequentially as the two individual components. All doses are coded and the test is performed under a code not known to the observer.

A stock suspension of sulindac is prepared by mixing 800 mg sulindac with 50 ml of an aqueous vehicle containing 2% by volume of Tween 80 ®, a pharmacological dispersant manufactured by Fisher Scientific Company and containing 100% polysorbate 80, and 1% by weight of Methocel ® MC powder, a suspending agent manufactured by DOW Chemical Company and containing 100% methylcellulose, in distilled water. The mixture is sonicated at 150 watts for 1–2 minutes with an ultrasound system, then shaken for two hours at 280 oscillations/minute with 15–20 gm of glass beads. The resultant suspension contains 16 mg/ml of sulindac; all dosing suspensions are prepared by dilution of the stock suspension with the Methocel ®/Tween 80 ® vehicle; the vehicle control is Methocel ®/Tween 80 ®. All suspensions are prepared fresh daily.

Stock solutions of nalbuphine HCl are prepared by dissolving dry nalbuphine hydrochloride powder with distilled water. All dosing solutions are prepared by dilution of the stock solution with distilled water; the vehicle control is distilled water.

As indicated above, the standard procedure based upon the prevention of phenyl-p-benzoquinone induced writhing in mice is utilized to detect and quantify the analgetic activity of compositions containing nalbuphine and sulindac.

Mice, intubated with various doses of nalbuphine hydrochloride, sulindac, combined doses of nalbuphine hydrochloride and sulindac, or vehicle, are injected intraperitoneally with a challenge dose of phenyl-p-benzoquinone 5 minutes prior to the designated observation period. The phenyl-p-benzoquinone is prepared as an 0.1 mg/ml solution in 5% by volume of ethanol in water; the writhing dose is 1.25 mg/kg injected in a volume of 0.25 ml/20 g. For scoring purposes a "writhe" is indicated by whole body stretching or contraction of the abdomen; mice are observed 10 minutes for the presence or absence of writhing beginning 5 minutes after receiving the phenyl-p-benzoquinone dose. Each mouse is used only once, then discarded. The alleviation of pain is quantified by determining the dosage at which 50% of the mice in a test group exhibit an analgesic response for the composition being tested. This dosage as described herein is referred to as the ED50. All ED50 values and their 95% confidence limits are determined numerically by the computer-assisted methods of Finney. [D. J. Finney, "Probit Analysis", Third Edition, Cambridge University Press, Cambridge, England, 1971].

In order to study the interaction between nalbuphine and sulindac, 5 precise dosage ratios of nalbuphine hydrochloride and sulindac are selected. Four or five coded doses of each selected combination are studied for analgesic effectiveness at 40 minutes using an experimental design which permits coding and complete randomization of the separate dosage forms tested. Altogether 35 separate dosage forms are used and each form is represented in each experimental session. The experiments are continued by running experimental sessions with an equal number of mice per group being tested until the total number, N, of mice tested per group is 30.

The nature of the analgetic interaction (addition, synergism, or antagonism) is determined by graphing the results in a Loewe isobologram [S. Loewe, *Pharm. Rev.* 9:237–242 (1957)]. The isobologram is a quantitative method for measuring interactions between drugs where dose-effect relationships are depicted in a multidimensional array with lines connecting dose pairs that are equieffective in relationship to a common pharmacological endpoint. In this instance, the antiphenylquinone writhing test is used to estimate a common level of analgesic activity (ED50 dose) for the two component drugs separately and for each fixed dose-ratio combination. In the isobolographic figure, areas of dose addition, synergism, and/or antagonism are clearly defined by reference to the theoretical "ED50 Addition Line." According to Loewe's isobolographic theory, ED50's falling under the curve (between the ED50 Addition Line and the origin) would represent unexpectedly enhanced analgetic activity and combination ED50's located above the line would represent unexpectedly diminished analgetic activity.

Most importantly, the isobolographic technique permits a full range of doses and dose combinations to be examined where the proportion of the first drug to the second actually varies from 0 to infinity, and to determine, by virtue of the graphical display, whether any one or more of the paired drug combinations displays unique pharmacological properties in comparison to the entire body of data generated. The isobologram is also valuable for organizing the data in a form which is easily amenable to statistical assessment of observed differences.

The synergistic interaction of nalbuphine hydrochloride and sulindac on phenyl-p-benzoquinone induced writhing in mice is demonstrated by the data in Table I and in the FIGURE, the Loewe isobologram. In the isobolographic figure, the analgetic effect of nalbuphine alone is presented in the ordinate, and that of sulindac alone is on the abscissa. The dotted lines radiating from the origin represent the exact fixed dosage ratios based on weight of nalbuphine HCl:sulindac in the ranges of 1:0.175 to 1:4.37. ED50 values are marked on the ordinate and abscissa, representing nalbuphine and sulindac alone, and on the dotted radial lines, representing the compositions of nalbuphine and sulindac at the fixed dosage ratios. The arrows extending above and below each ED50 point represent the 95% confidence limits of the ED50's.

As drawn in the FIGURE, the solid diagonal line joining the ED50 values of the two drugs given separately represents the "ED50 Addition Line," the theoretical line for simple additivity of drug effects which would be observed in the absence of a synergistic response. The drawing clearly shows that in the method of the invention, all of the tested fixed ratio compositions give unexpectedly enhanced analgetic activity since the ED50 values for each of these ratios fall below the line of simple additivity.

By utilizing an equieffective dose substitution model and a statistical regression analysis of all of the data, one can obtain a more reliable assessment of the existence of a synergistic property, in this case unexpectedly enhanced analgetic activity. The effects of two compounds are additive if the response to a dose of the two in combination does not change when a portion of one is removed from the mixture and replaced by an equipotent portion of the other. If such substitution increases the response, the mixing together of the compounds is said to potentiate their effects and synergism exists.

Consider ED50 doses of mixtures of X units of compound B with Y units of compound A, whose ED50 doses are $\beta$ and $\alpha$, respectively. Given the hypothesis of additivity, all doses of mixtures satisfying the straight line relation, $$Y = \alpha - (\alpha/\beta)X, \quad (1)$$

will be ED50 doses. To test the hypothesis of additivity, ED50 doses of mixtures are estimated through probit analysis of data from experiments run at various ratios of A to B. Linear and curvilinear regression models are fitted to the data to estimate the amounts of A in respective ED50 doses, given the amount of B, (or, conversely, the amount of B, given A). If a curvilinear regression fit the data significantly better than a straight line regression, the hypothesis of additivity is refuted and synergism exists for the two compounds for the property of interest.

Values of Y calculated from the straight line of Equation 1, and values of Y calculated from the curvilinear regression are plotted against X on an ED50 isobologram to describe the synergism.

It is convenient to standardize the units of dose such that 100 units of either compound alone is its respective estimated ED50 dose. The additivity hypothesis, then, will be represented by a straight line from 100 on the Y-axis to 100 on the X-axis on the isobologram, and Equation (1) becomes:

$$Y = 100 - X.$$

The isobologram in the FIGURE shows the straight line additivity hypothesis for nalbuphine HCl and sulindac 40 minutes post oral dosing in the mouse antiphenylquinone writhing test. Data were standardized to the ED50 doses of nalbuphine HCl (30.8 mg/kg) and sulindac (21.2 mg/kg). Synergism is demonstrated by the regression fitted to ED50 dose levels estimated by probit analysis. Its curvilinearity is statistically significant.

The regression is fitted to the data by the method of least squares. Residual squared deviations about the line of best fit are minimized in directions along lines from the origin through respective data points on the isobologram, these lines making angles with X-axis, $\tan^{-1}(Y/X)$. This is accomplished by a transformation prior to the regression analysis. Its inverse is applied to transform the coordinates of the regression curve back to the X,Y coordinates of the isobologram.

Let $D_r$ be an ED50 dose of a mixture of A and B, where r is the fraction of compound B in the mixture; i.e.

$$r = X/(X+Y).$$

It follows from Equation 1 that $$D_r = \frac{\alpha\beta}{\alpha r + \beta(1-r)}.$$

From the additivity hypothesis, the logarithms of the ED50 doses at various mixture ratios are a straight line function of (Log $D_r$). To test the hypothesis, polynomial regressions, as follows, are fitted to ED50 estimates from experimental data obtained at various mixture ratios:

$$F_r = \log D_r = b_0 + \sum_{i=1}^{K} b_i \left( \log \left[ \frac{\alpha\beta}{\alpha r + \beta(1-r)} \right] \right)^i \quad (2)$$

The additivity hypothesis is refuted if a polynomial of degree higher than one fit the data significantly better than a straight line, $$F_r = b_o + b_1 \left[ \log \left( \frac{\alpha\beta}{\alpha r + \beta(1-r)} \right) \right]$$

Since X and Y are uniquely determined by $F_r$ and r, the coordinates of the regression are transformed readily to the coordinates of the isobologram.

If data are scaled to ED50 dose levels of 100 standard dose units, Equation (2) becomes $$F_s = \log 100 = 2.$$

The additivity hypothesis implies that $F_s$ is independent of $r_s$, and may be tested by analysis of the regression model $$F_s = b_o + \sum_{i=1}^{K} b_i r_s^i, \quad (2.2)$$

the subscripts, s, indicating that the data are scaled. A statistically significant regression will refute the hypothesis.

The method of least squares utilizes jointly the information contained in all of the separate data points. Statistical significance of the curvilinearity of the regression model establishes the existence of synergism (or antagonism) of the compounds in the biological system studied. The parameters in the model describe its intensity over the range of mixture ratios, from 0 to 1, the nature of which is seen readily when the regression is plotted on the isobologram. This method was used to determine the best-fitting ED50 regression line through the seven (7) ED50 data points representing equivalent levels of analgetic activity for each of the five (5) dose-ratios and for nalbuphine and sulindac alone given in Table I. As shown in the isobologram plot of the FIG- URE, the calculated quartic polynomial "ED50 Regression Line" fits the data significantly better than the straight "ED50 Addition Line" as established by Fisher's F test, statistically significant at $p \leq 0.005$, to compare the goodness of fit between the straight line and curvilinear regressions. Thus, consistent with Loewe's isobolographic model, the hypothesis of anagetic additivity is refuted and analgetic synergism is established for all combinations of nalbuphine and sulindac.

By substitution of the expected analgetic activity of nalbuphine alone and sulindac alone from test results in other warm blooded mammals, it is possible to use the isobologram in conjunction with the correlation method discussed above to predict the equivalent range of maximum potentiating dosages for man. Thus utilizing the data of the present invention and the equivalent ratios in man, it is predicted that nalbuphine and sulindac would demonstrate analgetic potentiation over a range of doses exceeding 1:0.1 to 1:400.

As described above, all tests of statistical significance establishing the best fit regression equation for the experimental data and its difference from the ED50 Addition Line were carried out using stringent 95% confidence limits. The use of less stringent limits merely reinforces the conclusions.

It will be apparent that the instant specification and examples are set forth by way of illustration and not limitation, and that various modifications and changes may be made without departing from the spirit and scope of the present invention.

What is claimed is:

1. A pharmaceutical composition comprising a combination of (a) nalbuphine, or a pharmaceutically acceptable salt thereof, and (b) sulindac, or a pharmaceutically suitable salt thereof, in which the weight ratio of (a):(b) is from about 1:0.1 to about 1:400.

2. The composition of claim 1 wherein the weight ratio of (a):(b) is from about 1:0.1 to about 1:4.37.

3. The composition of claim 1, wherein the nalbuphine is present as the hydrochloride salt.

4. The composition of claim 1 wherein the sulindac is present as the sodium salt.

5. The composition of claim 1 which contains in addition a suitable pharmaceutical carrier.

6. The composition of claim 2 which contains in addition a suitable pharmaceutical carrier.

7. The composition of claim 3 which contains in addition a suitable pharmaceutical carrier.

8. The composition of claim 4 which contains in addition a suitable pharmaceutical carrier.

9. A method of alleviating pain in a mammal which comprises administering to said mammal affected with pain an effective analgesic amount of the composition of claim 1.

10. A method of alleviating pain in a mammal which comprises administering to said mammal affected with pain an effective analgesic amount of the composition of claim 2.

11. A method of alleviating pain in a mammal which comprises administering to said mammal affected with

TABLE I

ORAL NALBUPHINE/SULINDAC COMBINATIONS IN THE MOUSE ANTIPHENYLQUINONE WRITHING TEST 40 MIN (N-30 Mice/Dose)

| DRUG COMBINATIONS | DRUG DOSE (mg/kg) | | | ED50 AT 40 MIN (95% Confidence Limits) | |
|---|---|---|---|---|---|
| Nalbuphine HCl: Sulindac | Nalbuphine HCl | Sulindac | % MICE BLOCKED | Nalbuphine HCl | Sulindac |
| Control (0:0) | 0 | 0 | 10.0% | — | — |
| Nalbuphine | 5.45 | 0 | 16.7% | | |
| Only (1:0) | 10.9 | 0 | 40.0% | 30.8 | 0.0 |
| | 21.8 | 0 | 36.7% | (18.0–45.0) | |
| | 43.6 | 0 | 63.3% | | |
| | 87.2 | 0 | 90.0% | | |
| 1:0.175 | 4.54 | 0.792 | 10.0% | | |
| | 9.08 | 1.58 | 46.7% | 11.5 | 2.01 |
| | 18.2 | 3.17 | 76.7% | (8.42–14.4) | (1.47–2.51) |
| | 36.3 | 6.33 | 96.7% | | |
| | 72.7 | 12.7 | 100.0% | | |
| 1:0.435 | 3.63 | 1.58 | 13.3% | | |
| | 7.27 | 3.17 | 30.0% | 10.1 | 4.39 |
| | 14.5 | 6.33 | 83.3% | (7.52–12.4) | (3.27–5.38) |
| | 29.1 | 12.7 | 96.7% | | |
| | 58.1 | 25.3 | 100.0% | | |
| 1:0.872 | 2.73 | 2.38 | 6.7% | | |
| | 5.45 | 4.75 | 36.7% | 7.32 | 6.39 |
| | 10.9 | 9.5 | 80.0% | (5.49–8.99) | (4.79–7.85) |
| | 21.8 | 19.0 | 96.7% | | |
| | 43.6 | 38.0 | 100.0% | | |
| 1:1.74 | 1.82 | 3.17 | 30.0% | | |
| | 3.63 | 6.33 | 20.0% | 6.13 | 10.7 |
| | 7.27 | 12.7 | 83.3% | (0.00–364) | (0.00–633) |
| | 14.5 | 25.3 | 100.0% | | |
| | 29.1 | 50.7 | 100.0% | | |
| 1:4.37 | 0.908 | 3.96 | 10.0% | | |
| | 1.82 | 7.92 | 43.3% | 2.26 | 9.87 |
| | 3.63 | 15.8 | 80.0% | (1.70–2.75) | (7.41–12.0) |
| | 7.27 | 31.7 | 100.0% | | |
| | 14.5 | 63.3 | 100.0% | | |
| Sulindac | 0 | 4.75 | 20.0% | | |
| Only (0:1) | 0 | 9.5 | 20.0% | 0.0 | 21.2 |
| | 0 | 19.0 | 46.7% | | (16.6–25.2) |
| | 0 | 38.0 | 96.7% | | | pain an effective analgesic amount of the composition of claim 3.

12. A method of alleviating pain in a mammal which comprises administering to said mammal affected with pain an effective analgesic amount of the composition of claim 4.

13. A method of alleviating pain in a mammal which comprises administering to said mammal affected with pain an effective analgesic amount of the composition of claim 5.

14. A method of alleviating pain in a mammal which comprises administering to said mammal affected with pain an effective analgesic amount of the composition of claim 6.

15. A method of alleviating pain in a mammal which comprises administering to said mammal affected with pain an effective analgesic amount of the composition of claim 7.

16. A method of alleviating pain in a mammal which comprises administering to said mammal affected with pain an effective analgesic amount of the composition of claim 8.

* * * * *